(12) United States Patent
Smail

(10) Patent No.: US 10,238,469 B2
(45) Date of Patent: Mar. 26, 2019

(54) BONE REDUCTION BUR

(71) Applicant: Douglas Bruce Smail, Troy, NY (US)

(72) Inventor: Douglas Bruce Smail, Troy, NY (US)

( * ) Notice: Subject to any disclaimer, the term of this patent is extended or adjusted under 35 U.S.C. 154(b) by 175 days.

(21) Appl. No.: 15/054,595

(22) Filed: Feb. 26, 2016

(65) Prior Publication Data
US 2017/0245958 A1    Aug. 31, 2017

(51) Int. Cl.
*A61C 3/02* (2006.01)

(52) U.S. Cl.
CPC ..................... *A61C 3/02* (2013.01)

(58) Field of Classification Search
CPC ................................. A61C 3/02; A61C 3/025
USPC ........................ 407/29.13; 433/102, 165, 166
See application file for complete search history.

(56) References Cited

U.S. PATENT DOCUMENTS

| 843,273 | A * | 2/1907 | Homann ................. A61C 3/02 433/165 |
|---|---|---|---|
| D269,040 | S | 5/1983 | Deemer |
| 4,684,346 | A | 8/1987 | Martin |
| 5,931,841 | A * | 8/1999 | Ralph ................. A61B 17/1659 407/18 |
| 6,179,616 | B1 | 1/2001 | Danger |
| 6,565,356 | B2 | 5/2003 | Oyamada et al. |
| 7,347,692 | B2 | 3/2008 | Roetzer et al. |
| 8,784,421 | B2 | 7/2014 | Carrison et al. |
| 2002/0182565 | A1 * | 12/2002 | Senia ................. A61C 5/42 433/102 |
| 2006/0105293 | A1 | 5/2006 | Funato |
| 2007/0093841 | A1 | 4/2007 | Hoogland |
| 2007/0202461 | A1 * | 8/2007 | Wang ................. A61C 3/02 433/165 |
| 2009/0053674 | A1 * | 2/2009 | Danger ................. A61C 3/02 433/102 |
| 2009/0162812 | A1 | 6/2009 | Harouni |

FOREIGN PATENT DOCUMENTS

WO    WO2011098917 A1    8/2011

OTHER PUBLICATIONS

International Search Report and Written Opinion; dated May 19, 2017 for PCT Application No. PCT/US2017/017401.

* cited by examiner

*Primary Examiner* — Alan Snyder
(74) *Attorney, Agent, or Firm* — Mendelsohn Dunleavy, P.C.

(57) ABSTRACT

In one embodiment, a dental bur includes a proximal shank, an intermediate cutting section, and a smooth, rounded distal tip. The cutting section includes (i) a frustum-shaped portion connected at its larger-diameter end to the shank and (ii) a curved portion that provides a transition between the smaller-diameter end of the frustum-shaped portion and the rounded tip, where the outer surfaces of the frustum-shaped portion and the curved portion are both sufficiently abrasive to remove bone tissue due to the presence of surface grit and/or flutes that provide bone-cutting edges. The dental bur reduces and flattens the bone tissue of the maxillary and mandibular bones for surgical dental implants without unwanted soft tissue damage.

22 Claims, 3 Drawing Sheets

BONE REDUCTION BUR

BACKGROUND

Field of the Invention

The present invention relates to a surgical bone reduction bur and, in particular, to a dental bur used to prepare the site of a bone surface prior to dental implant placement.

Description of the Related Art

This section introduces aspects that may help facilitate a better understanding of the invention. Accordingly, the statements of this section are to be read in this light and are not to be understood as admissions about what is prior art or what is not prior art.

Dental implant surgery often requires the use of a surgical drill to prepare the topography of the jaw bone site prior to the placement of the dental implant. The gingiva are incised and pushed back to expose the jaw bone crest below. The surgical drill is then used to flatten the bone crest such that the bone no longer has ridges or irregularities that could otherwise result in implant misplacement and/or cleaning problems.

This dental implant procedure is often performed using burs that were originally designed for other dental procedures. U.S. Patent Application Publication No. 2006/0105293 A1 discloses such dental burs in FIGS. 2 and 3. Unfortunately, the tips of these dental burs have abrasive surfaces that can cause excessive damage to soft tissue, which damage can compromise healing.

Other burs exist that provide a protective tip for reducing damage to soft tissue. For example, U.S. Design Pat. No. D269,040 discloses dental burs that comprise an abrasive surface with a non-abrasive, rounded distal tip. However, these burs would not be useable for dental implant surgery, due to the shape of the rounded tip.

U.S. Patent Application Publication No. 2007/0093841 discloses a surgical drill bit having a blunted and smooth tip that provides protection to nerves, tissue, and dura. However, this drill bit, which was designed to remove bone within a spine, has a shape that would not result in flattening of the mandibular or maxillary bones nor would it provide the proper protection necessary for dental implant surgery.

SUMMARY

In one embodiment, the present invention is a dental bur comprising (i) a proximal shank, (ii) an intermediate cutting section connected to the shank, and (iii) a distal tip connected to the cutting section and having a smooth, rounded portion. The cutting section comprises (a) a frustum-shaped portion having a larger-diameter end and a smaller-diameter end and (b) a curved portion that provides a transition between (i) the smaller-diameter end of the frustum-shaped portion and (ii) the tip, wherein the outer surface of the frustum-shaped portion and the outer surface of the curved portion are both sufficiently abrasive to remove bone tissue.

BRIEF DESCRIPTION OF THE DRAWINGS

Embodiments of the invention will become more fully apparent from the following detailed description, the appended claims, and the accompanying drawings in which like reference numerals identify similar or identical elements.

DETAILED DESCRIPTION

Detailed illustrative embodiments of the present invention are disclosed herein. However, specific structural and functional details disclosed herein are merely representative for purposes of describing example embodiments of the present invention. The present invention may be embodied in many alternate forms and should not be construed as limited to only the embodiments set forth herein. Further, the terminology used herein is for the purpose of describing particular embodiments only and is not intended to be limiting of example embodiments of the invention.

As used herein, the singular forms "a," "an," and "the," are intended to include the plural forms as well, unless the context clearly indicates otherwise. It further will be understood that the terms "comprises," "comprising," "includes," and/or "including," specify the presence of stated features, steps, or components, but do not preclude the presence or addition of one or more other features, steps, or components. It also should be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Figure 1A:
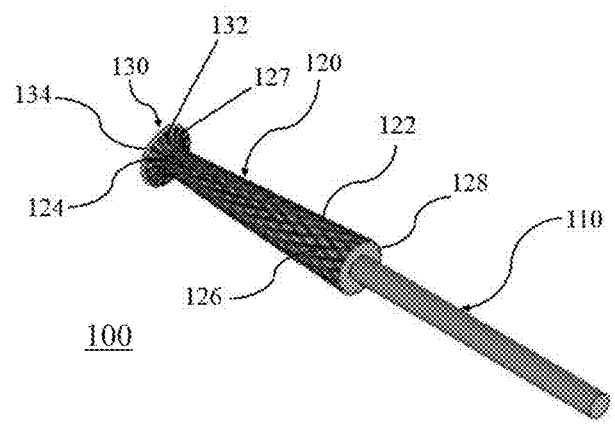
FIG. 1A is an isometric view of a dental bur according to one embodiment of the present disclosure.
Figure 1B:
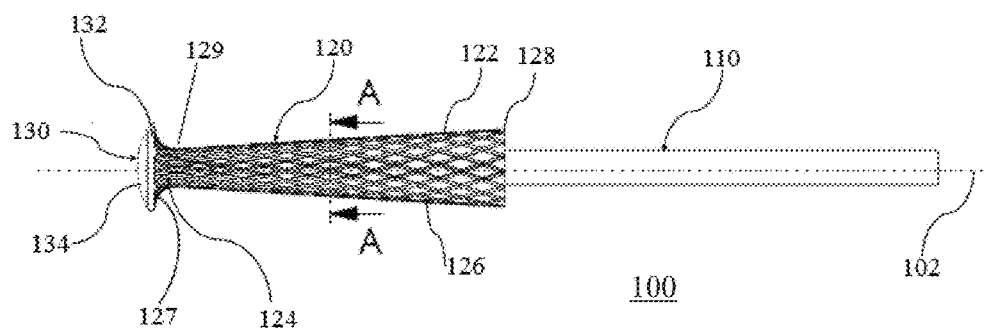
FIG. 1B is a side view of the dental bur of FIG. 1A.
Figure 1C:
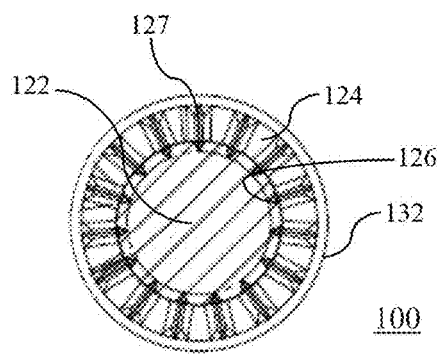
FIG. 1C is a cross-sectional view of the dental bur of FIGS. 1A-1B taken along line A-A of FIG. 1B.

FIG. 1A is an isometric view of a dental bur 100 according to one embodiment of the present disclosure. FIG. 1B is a side view of the dental bur 100, and FIG. 1C is a cross-sectional view of the dental bur 100 taken along line A-A of FIG. 1B. The dental bur 100 has a proximal shank 110, an intermediate cutting section 120, and a distal tip 130.

The shank 110, which has a solid (i.e., not hollow), cylindrical shape, is designed to be inserted into and retained within the chuck of a drill (not shown) that rotates the dental bur 100 about its longitudinal axis 102.

The cutting section 120 has (i) a solid, frustum-shaped portion 122 that abuts the shank 110 and (ii) a solid, curved portion 124 that provides a transition between the frustum-shaped portion 122 and the tip 130. The surface of the frustum-shaped portion 122 has two sets of helical flutes 126—one set running clockwise and the other counterclockwise—that intersect one another and extend along the frustum-shaped portion 122 to the curved portion 124, where non-helical flutes 127 extend longitudinally and radially, as shown in FIGS. 1A and 1C. The helical flutes 126 and non-helical flutes 127 both provide cutting edges that are designed to engage with and remove bone tissue. As shown in FIGS. 1A and 1B, the frustum-shaped portion 122 has a larger-diameter end 128 and a smaller-diameter end 129, where (i) the cutting section 120 is connected to the shank 110 at the larger-diameter end 128 of the frustum-shaped portion 122 and (ii) the curved portion 124 provides a transition between (i) the smaller-diameter end 129 of the frustum-shaped portion 122 and (ii) the tip 130.

The tip 130 comprises a solid, truncated cylindrical portion 132 and a solid, rounded portion 134, the surfaces of both of which being smooth (e.g., no flutes or grit) and therefore non-abrasive. The radius of curvature of the rounded portion 134 is sufficiently large such that the rounded portion 134 has the shape of a spherical cap or dome.

Note that the cross-sectional view of FIG. 1C shows the solid interior of the frustum-shaped portion 122 of the cutting section 120 with its helical flutes 126 as well as the curved portion 124 of the cutting section 120 with its non-helical flutes 127 and the edge of the cylindrical portion 132 of the tip 130.

Figure 2A:
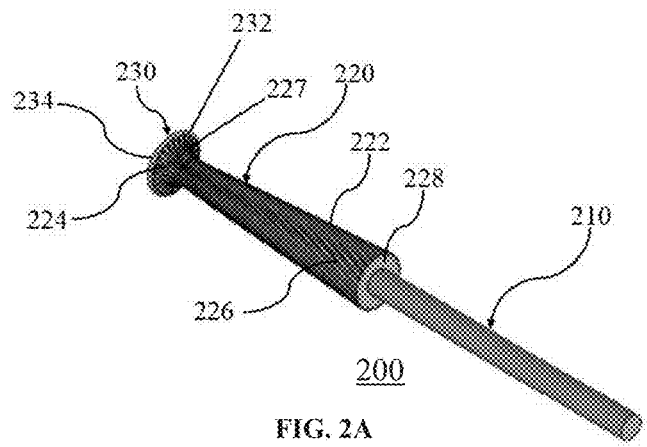
FIG. 2A is an isometric view of a dental bur according to another embodiment of the present disclosure.
Figure 2B:
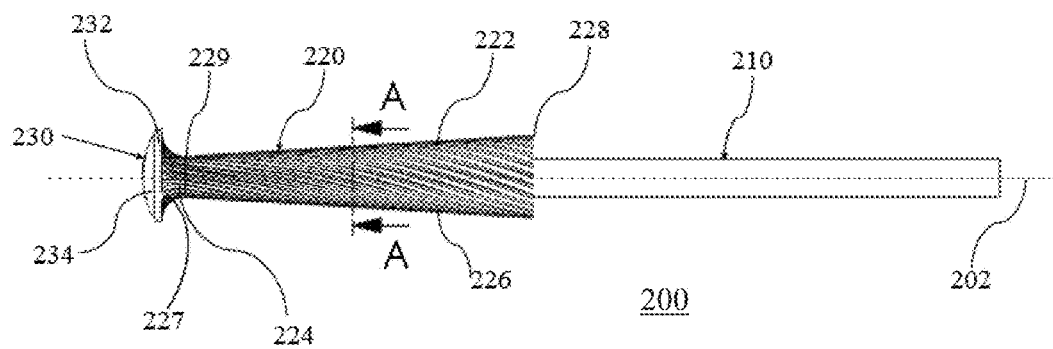
FIG. 2B is a side view of the dental bur of FIG. 2A.
Figure 2C:
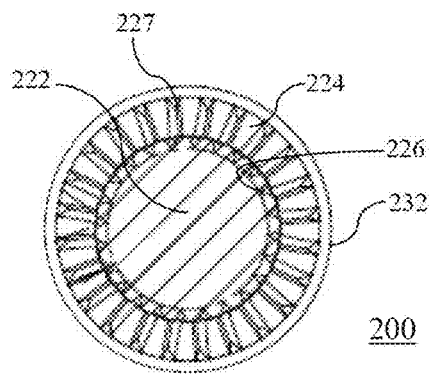
FIG. 2C is a cross-sectional view of the dental bur of FIGS. 2A-2B taken along line A-A of FIG. 2B.

FIG. 2A is an isometric view of a dental bur 200 according to another embodiment of the present disclosure. FIG. 2B is a side view of the dental bur 200, and FIG. 2C is a cross-sectional view of the dental bur 200 taken along line A-A of FIG. 2B. The dental bur 200 is analogous to the dental bur 100 of FIGS. 1A-1C with analogous features having similar labels. The main difference is that the dental bur 200 has a single set of non-intersecting helical flutes 226 rather than two intersecting sets of flutes 126 as in the dental bur 100, where the pitch (i.e., the distance between adjacent flutes) of the flutes 226 and 227 in the dental bur 200 is smaller than the pitch of the flutes 126 and 127 in the dental bur 100.

Dental burs of the present disclosure are primarily if not entirely made of a suitable metal, such as tungsten carbide for the tip with a surgical stainless steel shank, and may be manufactured using suitable techniques for manufacturing drill bits, such as forging and milling.

Note that, instead of or in addition to having flutes that provide cutting edges, the cutting section of a dental bur of the disclosure may have an abrasive surface, such as a surface coated with diamond particles or other types of grit that can wear down bone tissue.

Dental burs of the present disclosure are suited for reducing and flattening the bone tissue of the maxillary and mandibular bones for surgical dental procedures such as the All-on-4 dental implant procedure. The overall straight (i.e., ignoring the flutes) outer surface of the frustum-shaped portion 122/222 of the cutting section 120/220 enables a dental surgeon to achieve a flat crestal bone contour that is desired for preparing a dental implant site. The rounded, smooth portion 134/234 of the tip 130/230 displaces the soft gingiva tissue away from the cutting section 120/220, thereby reducing the amount of excessive damage. The curved portion 124/224 of the cutting section 120/220 provides a concave cutting surface that is designed to fit the corner of the crest and the inside wall of the jaw bone. This allows the dental bur 100/200 to move along the bony crest of the jaw, while reducing the desired bone tissue without unwanted soft tissue damage. This allows for efficient movability of the drill around the jaw from posterior to anterior and from side to side.

Figure 3:
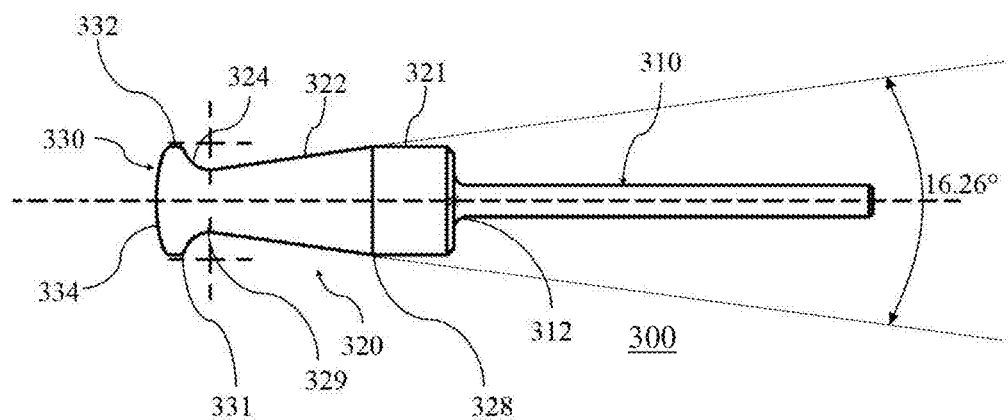
FIG. 3 is a cross-sectional side view of a dental bur according to yet another embodiment of the present disclosure.

FIG. 3 is a side view of a dental bur 300 according to yet another embodiment of the present disclosure. Although not depicted in FIG. 3, the dental bur 300 can be implemented with either two intersecting sets of flutes as in the dental bur 100 or a single set of non-intersecting flutes as in the dental bur 200.

Like the dental burs 100 and 200, the dental bur 300 has a cylindrical shank 310, a cutting section 320, and a rounded tip 230. Unlike the dental burs 100 and 200, in addition to having a frustum-shaped portion 322 and a curved portion 324, the cutting section 320 also has a cylindrical portion 321, which also has intersecting or non-intersecting flutes.

In one possible implementation, the dental bur 300 has the following dimensions:

Length of shank 310=31 mm;
Diameter of shank 310=2.32 mm;
Radius of curvature of curved portion 312 of shank 310=1 mm;
Length of cylindrical portion 321 of cutting section 320=6 mm;
Diameter of cylindrical portion 321 of cutting section 320=8 mm;
Length of frustum-shaped portion 322 of cutting section 320=12.02 mm;
Diameter of large-diameter end 328 of frustum-shaped portion 322 of cutting section 320=8 mm;
Angle of frustum-shaped portion 322 of cutting section 320=16.26°;
Radius of curvature of curved portion 324 of cutting section 320=2 mm;
Radius of curvature of curved portion 331 of tip 330=0.5 mm;
Diameter of cylindrical portion 332 of tip 330=8 mm;
Length of cylindrical portion 332 of tip 330=0.61 mm; and
Radius of curvature of rounded dome portion 334 of tip 330=32 mm.

Those skilled in the art will understand that these dimensions are merely illustrative of one particular implementation of the invention, and that other implementations may have one or more different dimensions. For example, the diameter of the shank 310 may be equal to the diameter of the cylindrical portion 321 of the cutting section 320. Note that, in alternative embodiments, the tip does not have a cylindrical portion 332. In those embodiments, the rounded portion 334 forms the entire tip 330.

Unless explicitly stated otherwise, each numerical value and range should be interpreted as being approximate as if the word "about" or "approximately" preceded the value or range.

It will be further understood that various changes in the details, materials, and arrangements of the parts which have been described and illustrated in order to explain embodiments of this invention may be made by those skilled in the art without departing from embodiments of the invention encompassed by the following claims.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

What is claimed is:

1. A bone reduction bur for preparing a site of a surface of a jaw bone prior to dental implant placement, said surgical bone reduction bur comprising:
a proximal shank;

an intermediate cutting section connected to the shank; and a distal tip connected to the cutting section, wherein:

the distal tip has a smooth, rounded portion shaped to displace gingival tissue away from the cutting section; and the cutting section comprises:

a frustum-shaped portion having a larger-diameter end and a smaller-diameter end; and a curved portion that extends from (i) the smaller-diameter end of the frustum-shaped portion to (ii) the tip, wherein the entire surface of the curved portion is concave, relative to a location outside the bone reduction bur and directly adjacent to the curved portion of the bone reduction bur, the curved portion is shaped to fit a corner of a crest and an inside wall of the jaw bone, and the outer surface of the frustum-shaped portion and the outer surface of the curved portion are both sufficiently abrasive to remove bone tissue from the site of the bone surface that is being prepared for dental implant placement.

2. The bone reduction bur of claim 1, wherein:

the outer surface of the frustum-shaped portion comprises a first set of helical flutes that define bone-cutting edges; and the outer surface of the curved portion comprises a set of non-helical flutes that define additional bone-cutting edges.

3. The bone reduction bur of claim 2, wherein the outer surface of the frustum-shaped portion further comprises a second set of helical flutes that define additional bone-cutting edges and intersect the first set of helical flutes.

4. The bone reduction bur of claim 1, wherein the shank has a cylindrical shape whose diameter is smaller than the diameter of the larger-diameter end of the frustum-shaped portion of the cutting section.

5. The bone reduction bur of claim 1, wherein the rounded portion of the tip has a shape of a spherical cap.

6. The bone reduction bur of claim 1, wherein the tip further comprises a truncated cylindrical portion connected between the rounded portion of the tip and the curved portion of the cutting section.

7. The bone reduction bur of claim 1, wherein:

the outer surface of the frustum-shaped portion comprises a first set of helical flutes that define bone-cutting edges;

the outer surface of the curved portion comprises a set of non-helical flutes that define additional bone-cutting edges;

the shank has a cylindrical shape whose diameter is smaller than the diameter of the larger-diameter end of the frustum-shaped portion of the cutting section; and the rounded portion of the tip has a shape of a spherical cap.

8. The bone reduction bur of claim 7, wherein the outer surface of the frustum-shaped portion further comprises a second set of helical flutes that define additional bone-cutting edges and intersect the first set of helical flutes.

9. The bone reduction bur of claim 7, wherein the tip further comprises a truncated cylindrical portion connected between the rounded portion of the tip and the curved portion of the cutting section.

10. The bone reduction bur of claim 1, wherein the cutting section further comprises a cylindrical portion connected to the larger-diameter end of the frustum-shaped portion, wherein the outer surface of the cylindrical portion is sufficiently abrasive to remove bone tissue.

11. The bone reduction bur of claim 10, wherein:

the outer surfaces of the cylindrical portion and the frustum-shaped portion are coated with grit that define bone-cutting edges; and the outer surface of the curved portion is coated with grit that defines additional bone-cutting edges.

12. The bone reduction bur of claim 11, wherein the outer surfaces of the cylindrical portion and the frustum-shaped portion further comprise a second set of helical flutes that define additional bone-cutting edges and intersect the first set of helical flutes.

13. The bone reduction bur of claim 10, wherein the rounded portion of the tip has a shape of a spherical cap.

14. The bone reduction bur of claim 13, wherein the outer surfaces of the cylindrical portion and the frustum-shaped portion comprise a first set of helical flutes that define bone-cutting edges;

the outer surface of the curved portion comprises a set of non-helical flutes that define additional bone-cutting edges;

the shank has a cylindrical shape whose diameter is smaller than the diameter of the cylindrical portion of the cutting section; and the outer surfaces of the cylindrical portion and the frustum-shaped portion further comprise a second set of helical flutes that define additional bone-cutting edges and intersect the first set of helical flutes.

15. The bone reduction bur of claim 13, wherein the tip further comprises a truncated cylindrical portion connected between the rounded portion of the tip and the curved portion of the cutting section.

16. The bone reduction bur of claim 1, wherein the outer surface of the frustum-shaped portion and the outer surface of the curved portion are both coated with grit.

17. The dental bur of claim 16, wherein the grit comprises diamond particles.

18. The bone reduction bur of claim 16, wherein the shank has a cylindrical shape whose diameter is smaller than the diameter of the larger-diameter end of the frustum-shaped portion of the cutting section.

19. The bone reduction bur of claim 16, wherein the rounded portion of the tip has a shape of a spherical cap.

20. The bone reduction bur of claim 16, wherein the tip further comprises a truncated cylindrical portion connected between the rounded portion of the tip and the curved portion of the cutting section, wherein the outer surface of the truncated cylindrical portion is not coated with grit.

21. The bone reduction bur of claim 16, wherein the cutting section further comprises a cylindrical portion connected to the larger-diameter end of the frustum-shaped portion, wherein the outer surface of the cylindrical portion is coated with diamond particles.

22. The bone reduction bur of claim 16, wherein:

the grit comprises diamond particles;

the shank has a cylindrical shape whose diameter is smaller than the diameter of the larger-diameter end of the frustum-shaped portion of the cutting section;

the rounded portion of the tip has a shape of a spherical cap;

the tip further comprises a truncated cylindrical portion connected between the rounded portion of the tip and the curved portion of the cutting section, wherein the outer surface of the truncated cylindrical portion is not coated with grit; and the cutting section further comprises a cylindrical portion connected to the larger-diameter end of the frustum-shaped portion, wherein the outer surface of the cylindrical portion is coated with diamond particles.

* * * * *